United States Patent [19]
Crain et al.

[11] Patent Number: 5,585,348

[45] Date of Patent: Dec. 17, 1996

[54] USE OF EXCITATORY OPIOID RECEPTOR ANTAGONISTS TO PREVENT GROWTH FACTOR-INDUCED HYPERALGESIA

[75] Inventors: Stanley M. Crain, Leonia, N.J.; Ke-fei Shen, Flushing, N.Y.; John A. Kessler, New Canaan, Conn.; Stuart C. Apfel, West Hempstead, N.Y.

[73] Assignee: Albert Einstein College of Medicine of Yeshiva University, a Division of Yeshiva University, Bronx, N.Y.

[21] Appl. No.: 106,401

[22] Filed: Aug. 13, 1993

Related U.S. Application Data

[63] Continuation-in-part of Ser. No. 17,349, Feb. 10, 1993, abandoned, and a continuation-in-part of Ser. No. 97,460, Jul. 27, 1993, Pat. No. 5,472,943.

[51] Int. Cl.⁶ .................................................. A61K 38/00
[52] U.S. Cl. .................................................. 514/12; 514/21
[58] Field of Search ........................................ 514/12, 21

[56] References Cited

PUBLICATIONS

Apfel et al., Ann. Neurol. 29: 87–90 (1991).
Shen, K. F. and S. M. Crain, Brain Research, 491 pp. 227–242 (1989).
R. Levi–Montalcini et al., Progress in Neuro Endocrine Immunology, vol. 3, No. 1, pp. 1–10 (1991).
Arts, et al., Pharmacol. Biochem. Behav., in press (1993).
Lewin et al., J. Neurosci., vol. 13, pp. 2136–2148 (1993).
Apfel et al., Brain Res., in press (1993).
Shen and Crain, Brain Res., in press, (1993).
Shen and Crain, Soc. Neurosci. Abstr., in press (1993).
Hamann et al., J. Pharmacol. Exp. Ther., vol. 261, pp. 707–715 (1992).
Fujimoto et al., FASEB J., vol. 6, A1302 (1992).
Waite et al., Soc. Neurosci. Abstr., vol. 18, p. 690 (1992).
Meakin et al., Trends Neurosci., vol. 15, pp. 323–331 (1992).
Apfel et al., Ann. Neurol., vol. 29, pp. 87–90 (1991).
Levi et al., Ann. Rev. Pharmacol., vol. 31, pp. 205–228 (1991).
Shen and Crain, Brain Res., vol. 59, pp. 130–138 (1991).
Westcamp et al., Neuron, vol. 6, pp. 649–663 (1991).
Hempstead et al., Nature, vol. 6, pp. 649–663 (1991).
Kaplan et al., Science, vol. 252, pp. 554–558 (1991).
Nikodijevic et al., J. Neurosci. Res., vol. 26, pp. 288–295 (1990).
Levi–Montalcini et al., Prog. in NeuroEndocrineImmunol., vol. 3, pp. 1–10 (1990).
Crain and Shen, Trends Pharmacol. Sci., vol. 11, pp. 77–81 (1990).
Shen and Crain, Brain Res., vol. 525, pp. 225–231 (1990).
Lazarovici et al., J. Neurosci. Res., vol. 23, pp. 1–8 (1989).
Shen and Crain, Brain Res., vol. 491, pp. 227–242 (1989).
Fujimoto et al., J. Pharmacol. Exp. Ther., vol. 251, pp. 1045–1052 (1989).
Fujimoto et al., Neuropharmacol., vol. 29, pp. 609–617 (1989).
Holz et al., J. Neurosci., vol. 8, pp. 463–471 (1988).
Kayser et al., Brain Res., vol. 414, pp. 155–157 (1987).
Chalazonitis et al., Proc. Nat'l. Acad. Sci. USA, vol. 84, pp. 289–293 (1987).
Duggan et al., Brain Res., vol. 403, pp. 345–349 (1987).
Mazurek et al., FEBS Lett., vol. 198, pp. 315–320 (1986).
Helme et al., Neurosci. Lett., vol. 198, pp. 463–471 (1986).
Basbaum et al., J. Neurosci., vol. 6, pp. 127–133 (1986).
Sujiyama et al., Arch. Oral Biol., vol. 30, pp. 93–95 (1985).
Rice et al., J. Neurochem., vol. 44, pp. 1588–1592 (1985).
Chandler et al., J. Biol. Chem., vol. 259, pp. 649–663 (1984).
Wu et al., Life Sci., vol. 33, pp. 1831–1838 (1983).
Peterson and Crain, Science, vol. 217, p. 337 (1982).
Bruni et al., FEBS Lett., vol. 138, pp. 190–192 (1982).
Greene et al., Ann. Rev. Neurosci., vol. 3, pp. 353–402 (1980).
Skaper et al., J. Neurochem., vol. 32, pp. 1845–1851 (1979).
Mudge et al., Proc. Nat'l. Acad. Sci. USA, vol. 76, pp. 526–530 (1979).
Schubert et al., Nature, vol. 273, pp. 718–723 (1978).
Jessel et al., Nature, vol. 268, pp. 549–551 (1977).
Nikodijevic et al., Proc. Nat'l. Acad. SCi. USA, vol. 72, pp. 4769–4771 (1975).

*Primary Examiner*—Howard E. Schain
*Assistant Examiner*—P. Lynn Touzeau
*Attorney, Agent, or Firm*—Amster, Rothstein & Ebenstein

[57] ABSTRACT

This invention relates to a method of preventing hyperalgesia and other undesirable side-effects associated with the administration of growth factor, including nerve growth factor, utilizing an antagonist capable of inactivating excitatory opioid receptor-mediated functions on neurons in the nociceptive pathway. In addition, this invention relates to a composition comprising a growth factor and an antagonist capable of inactivating excitatory opioid receptor-mediated functions on neurons in the nociceptive pathway.

8 Claims, 11 Drawing Sheets

1. BSS
2. NGF 0.1nM 3. anti-NGFR 50ng/ml
4. anti-NGFR + NGF 0.1nM 20 mV
10 ms

1. NTI 10nM
2. NTI + NGF 1nM

3. B-FNA 10nM
4. B-FNA + NGF 1nM 5. nor-BNI 10nM
6. nor-BNI + NGF 1nM 20 mV
10 ms 1. BSS
2. NGF 0.1nM 3. CTX-A 0.1ug/ml
4. CTX-A + NGF 0.1nM

* Signifies that this group differs from control with p<0.05 and from NGF+Nal+Nalt with p<0.01 by ANOVA.

\* Signifies that this group differs from both control and NorBNI with p<0.001 by ANOVA

USE OF EXCITATORY OPIOID RECEPTOR ANTAGONISTS TO PREVENT GROWTH FACTOR-INDUCED HYPERALGESIA

STATEMENT OF GOVERNMENT INTEREST

This invention was made with government support under NIDA Research Grant Number DA 02031 and NIH Grant Number R01 ES05752-02. As such, the government has certain rights in the invention.

CROSS-REFERENCE TO RELATED APPLICATIONS

This Application is a Continuation-In-Part of application Ser. No. 08/017,349 now abandoned, filed Feb. 10, 1993, entitled USE OF GROWTH FACTORS TO TREAT DRUG INDUCED NEUROPATHY, and a Continuation-In-Part of application Ser. No. 08/097,460, U.S. Pat. No. 5472943, (not yet assigned) filed Jul. 27, 1993, entitled METHOD OF SIMULTANEOUSLY ENHANCING ANALGESIC POTENCY AND ATTENUATING DEPENDENCE LIABILITY CAUSED BY MORPHINE AND OTHER OPIOID AGONISTS, which applications are incorporated herein by reference.

FIELD OF THE INVENTION

This invention relates to a method of preventing or attenuating hyperalgesia and other undesirable side-effects associated with the administration of nerve growth factor or related growth factors. Specifically, this invention relates to the pretreatment with or co-administration (with growth factor) of an antagonist capable of inactivating excitatory opioid receptor-mediated functions on neurons in the nociceptive pathway. In addition, this invention relates to a composition comprising a growth factor and an antagonist capable of inactivating excitatory opioid receptor-mediated functions on neurons in the nociceptive pathway.

BACKGROUND OF THE INVENTION

Several anti-tumor drugs, including taxol, cisplatin and vincristine, when administered, have adverse side-effects on individuals, including toxic sensory or sensorimotor neuropathy and neuronal dysfunction. For example, taxol is a plant alkaloid that promotes the assembly of microtubules and stabilizes them. Clinical trials have demonstrated taxol's antineoplastic activity against solid tumors, including metastatic melanoma. However, taxol, cisplatin and vincristine cause toxic sensory neuropathy, and are cytotoxic to dorsal root ganglion neurons. Additionally, certain anti-viral drugs, including dideoxycytidine and dideoxyinosine, when administered, cause toxic neuropathy.

Co-treatment of individuals with the above-discussed anti-tumor and antiviral drugs, along with growth factors, including nerve growth factor, has previously been shown to prevent neuronal death in in vitro experiments (see Peterson and Crain, *Science*, Vol. 217, p. 337 (1982)). In addition, it has been demonstrated that administration of nerve growth factor to rat and mouse models of taxol (see Apfel et al., *Ann. Neurol.*, Vol. 29, pp. 87–90 (1991)) and diabetic neuropathy (see Apfel et al., *Brain Res.*, In Press (1993)) prevents neuropathy. However, nerve growth factor and other growth factors have been shown to cause hyperalgesic side-effects.

Nerve growth factor (NGF) has been shown to elicit rapid biochemical and structural changes in nerve cells (see Greene et al., *Ann. Rev. Neurosci.*, Vol. 3, pp. 353–402 (1980) and Levi et al., *Ann. Rev. Pharmacol.*, Vol. 31, pp. 205–228 (1991)). For example, the application of NGF to PC12 cells results in increased cystolic $Ca^{2+}$ concentration within minutes, due to enhanced $Ca^{2+}$ influx as well as release from internal stores (see Lazarovici et al., *J. Neurosci. Res.*, Vol. 23, pp. 1–8 (1989)).

Furthermore, nerve growth factor has been shown to increase the $Ca^{2+}$-dependent release of dopamine and norepinephrine from PC12 cells within a few minutes (see Nikodijevic et al., *J. Neurosci. Res.*, Vol. 26, pp. 288–295 (1990)), and the release of histamine from mast cells within minutes in vitro in the presence of lysophosphatidyl serine (see Bruni et al., *FEBS Lett.*, Vol. 138, pp. 190–192 (1982); Sujiyama et al., *Arch. Oral Biol.*, Vol. 30, pp. 93–95 (1985); and Mazurek et al., *FEBS Lett.*, Vol. 198, pp. 315–320 (1986)). Nerve growth factor has also been found to enhance endogenously released adenosine effects on PC12 cells (see Rice et al., *J. Neurochem.*, Vol. 44, pp. 1588–1592 (1985)), and may account for previous reports that nerve growth factor rapidly stimulates cyclic AMP levels in PC12 and other types of neurons (see Nikodijevic et al., *Proc. Nat'l. Acad. Sci. USA*, Vol. 72, pp. 4769–4771 (1975); Schubert et al., *Nature*, Vol. 273, pp. 718–723 (1978); and Skaper et al., *J. Neurochem.*, Vol. 32, pp. 1845–1851 (1979)). Finally, it has been reported that nerve growth factor administration causes hyperalgesic response in rodents (see Levi-Montalcini et al., *Prog. in NeuroEndocrineImmunol.*, Vol. 3, pp. 1–10 (1990) and Lewin et al., *J. Neurosci.*, Vol. 13, pp. 2136–2148 (1993)).

Because nerve growth factor and other growth factors are of great use in limiting toxic sensory neuropathy and neuronal dysfunction, a great need exists to prevent hyperalgesia and other undesirable side-effects caused by the administration of nerve growth factor and other growth factors.

It is therefore an object of this invention to provide a method of preventing hyperalgesia and other undesirable side-effects caused by the administration of nerve growth factor and other growth factors.

It is a further object of this invention to provide a composition capable of simultaneously preventing toxic sensory neuropathy and neuronal dysfunction and preventing growth factor-associated hyperalgesia.

SUMMARY OF THE INVENTION

This invention is directed to a method of preventing hyperalgesia and other undesirable opioid receptor-mediated side-effects associated with the administration of growth factors, including nerve growth factor. An antagonist capable of inactivating excitatory opioid receptor-mediated functions on neurons is co-administered along with said growth factor. Alternatively, said antagonist is administered prior to administering said growth factor. This invention is further directed to a composition comprising a growth factor and an antagonist capable of inactivating excitatory opioid receptors on neurons.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein:

FIG. 2 represents the blocking of nerve growth factor-induced APD prolongation by pretreatment of DRG neurons with the opioid receptor antagonist naloxone or the specific kappa opioid receptor antagonist nor-binaltorphimine;

FIG. 3 represents the blocking of nerve growth factor-induced APD prolongation by pretreatment of DRG neurons with cholera toxin A or B subunits;

DETAILED DESCRIPTION OF THE INVENTION

Figure 1A:
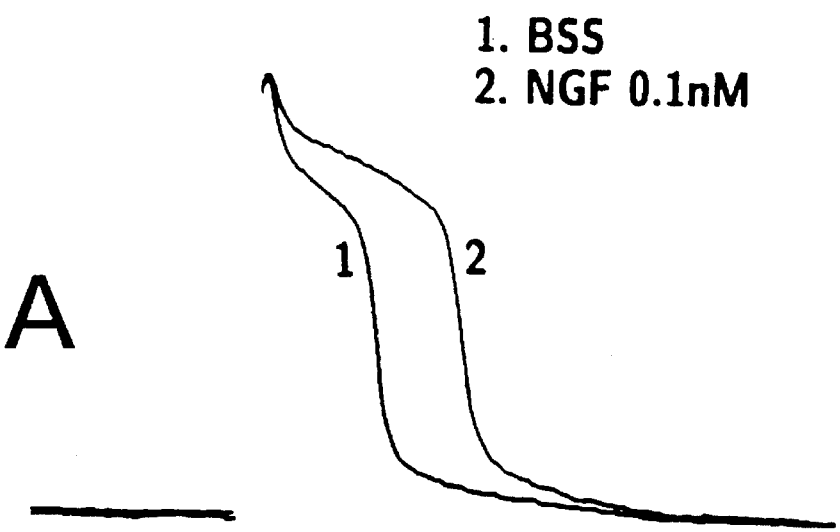
FIG. 1 represents the blocking of the nerve growth factor-induced APD prolongation by pretreatment of DRG neurons with antibodies to nerve growth factor receptors.

This invention is directed to a method of preventing hyperalgesia and other undesirable opioid receptor-mediated side-effects associated with the administration of growth factors. An antagonist capable of inactivating excitatory opioid receptor-mediated functions on neurons is co-administered along with said growth factors. Alternatively, said antagonist is administered prior to administering growth factors. This invention is also directed to a composition comprising a growth factor and an antagonist capable of inactivating excitatory opioid receptor-mediated functions on neurons in the nociceptive pathway.

As discussed hereinabove, growth factors, including nerve growth factor, may be administered to reduce or prevent toxic sensory or sensorimotor neuropathy and neuronal dysfunction. Growth factors of the invention include nerve growth factor, ciliary-derived neurotrophic factor, brain-derived neurotrophic factor, neurotrophin-3, neurotrophin 4-5, fibroblast growth factor, epidermal growth factor, transforming growth factor α and transforming growth factor β.

However, nerve growth factor has been shown to cause hyperalgesia side-effects. The inventors have discovered that in order to prevent hyperalgesia and other undesirable side-effects associated with the administration of growth factor, certain compounds can be either co-administered with said growth factor or administered prior to administration of said growth factor in order to prevent hyperalgesia and other undesirable side-effects caused by the growth factor. These compounds are antagonists which are capable of inactivating excitatory opioid receptor-mediated functions on neurons in the nociceptive pathway. Specifically, the antagonists of this invention include naloxone, naltrexone and nor-binaltorphimine (which block both inhibitory and excitatory opioid receptors; see Shen and Crain, *Brain Res.*, Vol. 491, pp. 227–242 (1989)), etorphine, dihydroetorphine and diprenorphine (which can selectively block excitatory opioid receptors see Shen and Crain, *Brain Res.*, In Press, (1993)) and cholera toxin A and B subunits. The excitatory opioid receptors inactivated by the antagonists of the invention include kappa subtype opioid receptors.

The range of doses of nerve growth factor to be administered is 0.1–1 µg/kg. The ranges of doses of the antagonists are for naloxone, 0.1–0.2 mg intravenously, for naltrexone, 25–50 mg orally, and for nor-binaltorphimine, 5 µg/kg-mg/kg. Tissue culture studies suggest that the antagonists etorphine, dihydroetorphine and diprenorphine can be administered at much lower doses, less than 1 µg/kg. The modes of administration of said antagonist and/or growth factor includes sublingual, intramuscular, intradermal, subcutaneous, intraperitoneal, intravenous and inhalation administration.

The inventors have discovered that nerve growth factor stimulates the release of low concentrations of endogenous opioids, such as dynorphin, from dorsal root ganglion (DRG) neurons. These endogenous opioids activate kappa excitatory receptors, which results in hyperalgesia. The inventors have further discovered that this nerve growth factor-induced hyperalgesia can be blocked by pretreatment of an individual with an antagonist of the invention. Alternatively, the antagonist of the invention can be co-administered along with nerve growth factor in order to block nerve growth factor-induced hyperalgesia.

Tests on Sensory Neurons in Tissue Cultures

The inventors have performed in vitro studies in which low concentrations of nerve growth factor were applied acutely to mouse sensory dorsal-root ganglion (DRG) neurons in long-term organotypic cultures. In addition, the inventors utilized eletrophysiologic testing to determine that pretreatment of DRG neurons with monoclonal antibodies to rodent NGF receptors, naloxone, naltrexone, nor-binaltorphimine and cholera toxin A and B subunits block the rapid prolongation of the action potential duration caused by nerve growth factor (see Shen and Crain, *Soc. Neurosci. Abstr.*, In Press (1993)).

In order to prepare tissue cultures of dorsal root ganglion (DRG) neurons, organotypic DRG-cord explants were prepared by dissecting transverse sections of spinal cord with attached DRGs from 13-day-old fetal mice (CD-1, Charles River). The explants were grown on collagen-coated coverslips in Maximow slide chambers and fed with Eagle's minimal essential medium supplemented with 25% fetal bovine serum, 10% chick embryo extract, 2 mM glutamine, 0.6% glucose and 10 mM HEPES buffer. During the first week in vitro the medium was supplemented with NGF (7S) at a concentration of 5 nM (about 50 units/ml) to enhance survival and growth of the fetal mouse DRG neurons. Cultures were fed twice weekly and maintained at 34° C. for electrophysiologic study after 3–7 weeks in vitro.

In order to perform electrophysiology tests, culture coverslips were transferred to a small recording chamber containing about 1 ml of Hanks' balanced salt solution (BSS) supplemented with 4 mM $Ca^{2+}$ and 5 $Ba^{2+}$ (i.e., Ca,Ba/BSS). The addition of $Ba^{3+}$ and high $Ca^{2+}$ enhanced inward $Ca^{2+}$ current, and $Ba^{2+}$ suppressed delayed rectifying $K^+$ current, thereby prolonging the action potential duration (APD) and providing a prominent baseline response for pharmacologic tests. HEPES (10 mM pH 7.3) was used to replace the usual bicarbonate and phosphate buffers to prevent $Ba^{2+}$ and $Ca^{2+}$ precipitation. Intracellular recordings were made from DRG perikarya selected at random within each ganglion. Tests were made primarily on medium- and small-diameter cells (about 10–30 μm) which generally showed longer APDs and were more likely to include nociceptive DRG neurons. The micropipettes were filled with 3M KCl (having a resistance of about 80–120 Megohm) and were connected via a chlorized silver wire to a neutralized input-capacity preamplifier (Axoclamp 2A) for current-clamp recording. After impalement of a DRG neuron, brief (2 minute) depolarizing current pulses were applied via the recording electrode to evoke action potentials (APs) at a frequency of 0.1 Hz. Recordings of the membrane resting potential (RP) and AP were stored on a floppy disc using the P-clamp program (Axon Instruments) in a microcomputer (IBM AT-compatible).

Drugs were applied by bath perfusion with a manually operated push-pull syringe system at a rate of 2–3 ml/min. Perfusion of NGF or other test agents was begun after the AP and RP of the neuron reached a stable condition during >4 minute pretest periods in control Ca,Ba/BSS. Tests were made on cells with RPs >60 mV and a holding current was generally applied to maintain the baseline membrane potential at about −70 mV. NGF-mediated changes in the APD were considered significant if the APD alteration was >10% of the control value. The APD was measured as the time between the peak of the APD and the inflection point on the repolarizing phase.

The following drugs were utilized: NGF 7S (Collaborative Research); NGF 2.5S and rat anti-NGF-receptor antibody (192-IgG, Boehringer Mannheim); dynorphin (1–13), and [D-Ala$_2$, D-Leu$^5$] enkephalin (DADLE) (Sigma); cholera toxin A subunit and B subunit (List); naloxone (Endo); (+)naloxone (NIDA); nor-binaltorphimine HCl, naltrindole HCl and beta-funaltrexamine HCl (Research Biochemical).

Stock solutions were prepared in distilled water (about 1 mM) and stored frozen. Nerve growth factor (NGF) was prepared in Eagle's minimal essential medium supplemented with 25% fetal bovine serum and aliquots were stored at −70° C. and not refrozen after thawing. Cholera toxins were stored at 4° C. Cholera toxin-B subunit was heated to 56° C. for 30 minutes to inactivate possible contamination with cholera toxin-A subunit. Stock solutions were diluted with the bath solution to desired test concentrations, discarding pipette tips after each successive dilution to ensure accuracy of extremely low (pM-fM) concentrations. Data analysis for determining significant differences was carried out with paired t test.

Electrophysiologic tests were carried out on long-term cultures of DRG-cord explants to determine if NGF could elicit rapid alterations in the APD of DRG neurons such as occurs during acute application of monoamines, opioids and other neurotransmitters. It was discovered by the inventors that NGF rapidly prolongs the APD of DRG neurons. In contrast to the APD shortening observed after chronic NGF treatment of DRG neurons (see Chalazonitis et al., *Proc. Nat'l. Acad. Sci. USA*, Vol. 84, pp. 289–293 (1987)), the inventors have learned that acute application of similar and even much lower concentrations of NGF (7S or 2.5S) elicit unexpected prolongation of the APD within a few minutes.

Figure 1B:
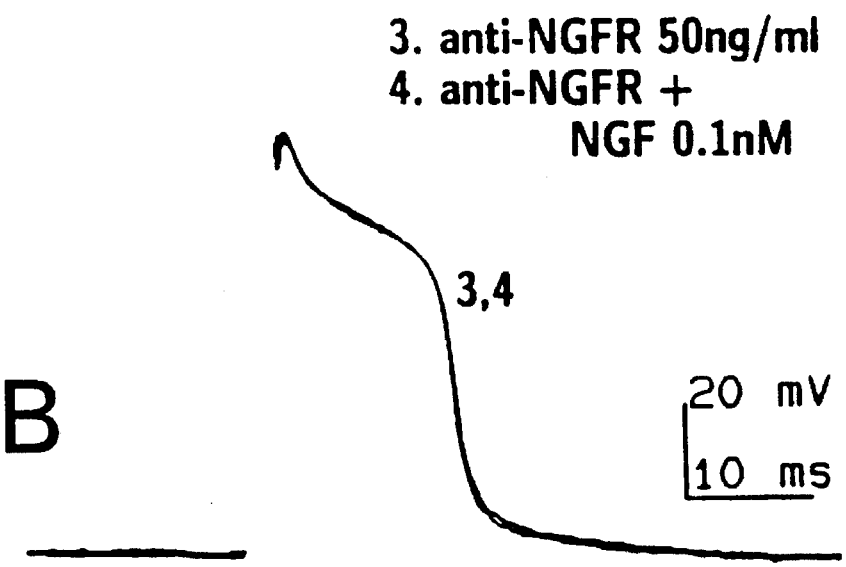
Figure 2A:
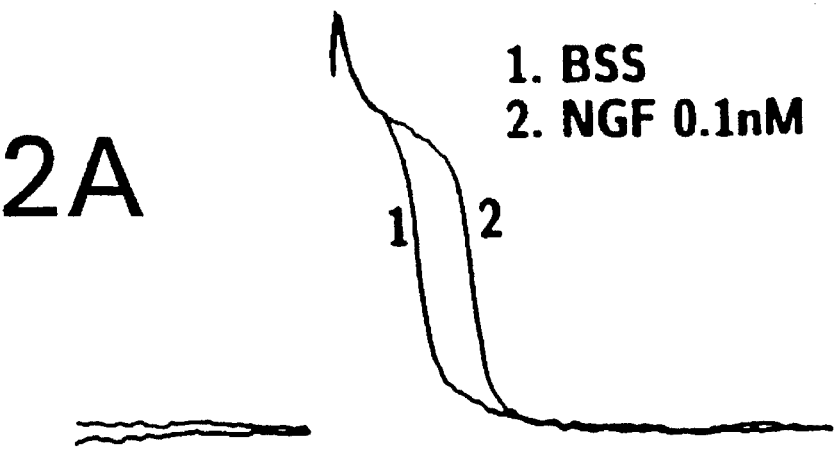
FIG. 2 is comprised of FIG. 2A and FIG. 2B.
Figure 2B:
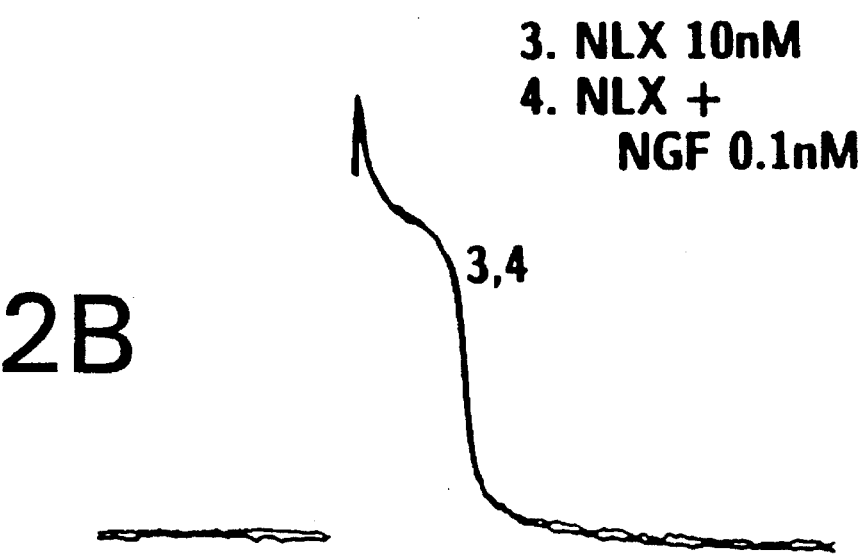
Figure 2C:
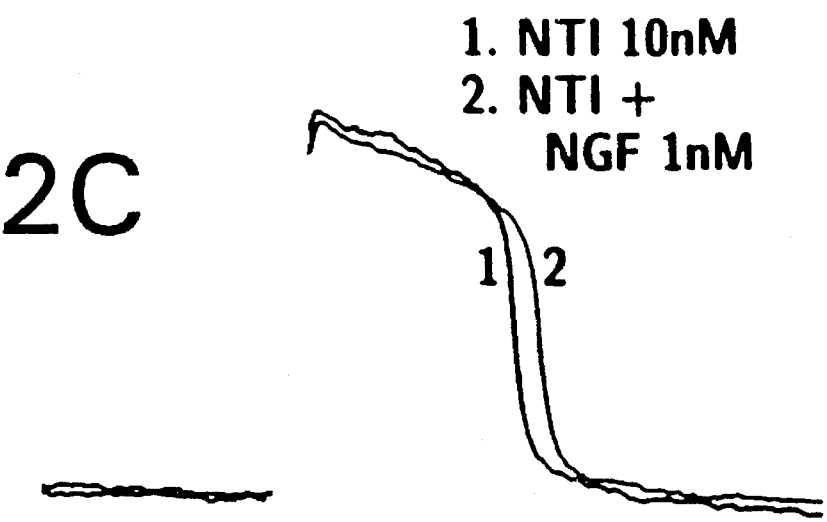
Figure 2D:
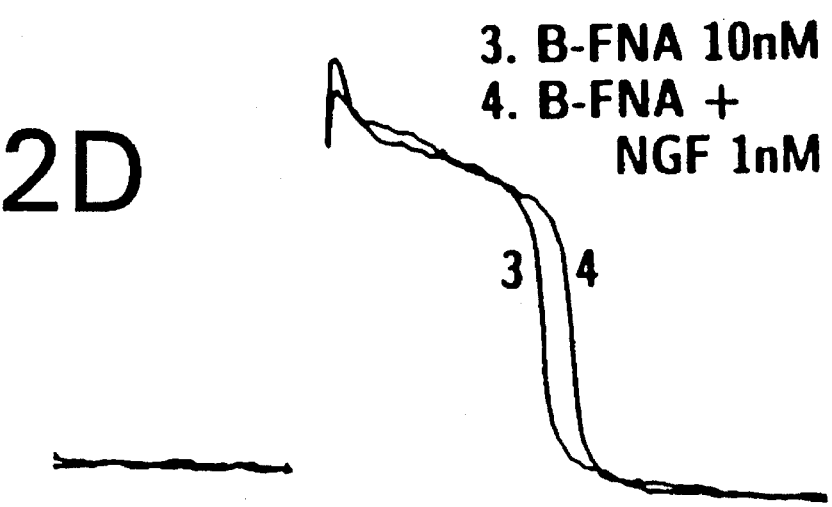
Figure 2E:
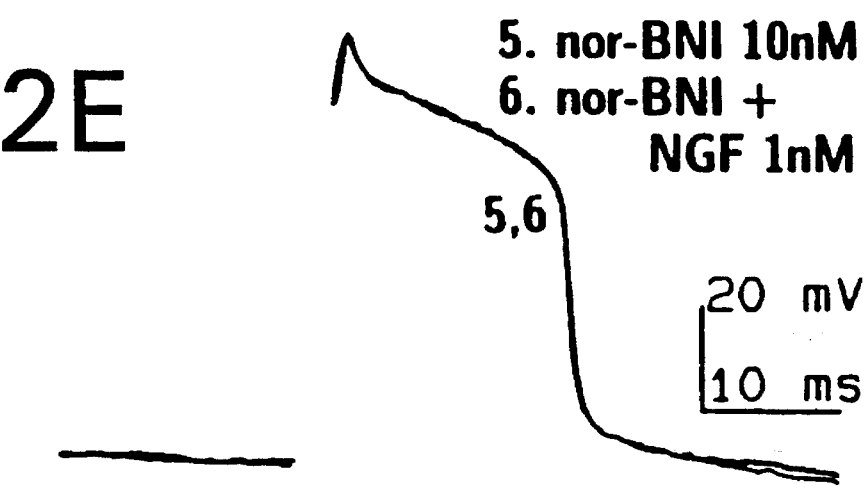

FIG. 1 demonstrates that NGF-evoked prolongation of the action potential duration (APD) of cultured DRG neurons is blocked by pretreatment with antibodies to NGF receptors (anti-NGFR), whereas perfusate from NGF-stimulated DRG explant can still prolong the APD of anti-NGFR-treated cells. Record 1 shows the action potential (AP) generated by a DRG neuron in balanced salt solution containing 5 mM $Ca^{2+}$ and 5 mM $Ba^{2+}$ (BSS) in response to brief (2 msec) depolarizing current pulse. The same 2 msec stimulus was used in all subsequent records. Record 2 shows that the APD is prolonged within 5 minutes after bath application of 0.1 nM NGF(7S). Record 3 shows that after BSS rinse and introduction of anti-NGFR (192-IgG, 50 ng/ml), APD shortens and is then stably maintained (for about 10 minutes) prior to additional tests. Record 4 shows that the application of NGF (0.1 nM) in the presence of anti-NGFR is no longer effective in prolonging the APD (5 minute test). Records in this and the subsequent Figures are from DRG neurons in DRG-spinal cord explants tested at 3–5 weeks in vitro. All acute tests were monitored for 5 minute periods.

It was found that NGF is effective in prolonging the APD of many DRG neurons (by 20–120%) at remarkably low concentrations: in 78% of the cells tested at 0.1–1 pM (n=18; $p<0.001$); in 88% of the cells tested at 10–100 pM (n=58; $p<0.001$); and in 93% of the cells tested at 1–10 nM (n=41; $p<0.001$). No significant evidence of NGF-induced APD shortening was observed during these acute tests. The magnitude of the APD prolongation elicited by acute application of NGF did not show significant dose-dependent increases when tested at concentrations from 1 pM to 10 nM.

The 2.5S form of NGF elicited similar effects on the APD as observed with the 7S form, except that the APD prolongation during sustained exposure to NGF-2.5S tended to attenuate more rapidly, often within 5 minutes. After washout of either form of NGF, the APD returned to control values within 5 to 10 minutes. These excitatory effects of NGF on DRG neurons were mediated by activation of NGF receptors since they were blocked after pretreatment of the cells with monoclonal antibodies to rodent NGF receptors (anti-NGFR) in 5 out of 5 cells treated with 5 μg/ml anti-NGFR and in 2 out of 3 cells treated with 50 ng/ml anti-NGFR.

The inventors have discovered that certain opioid antagonists block NGF-induced APD prolongation. Since it was previously demonstrated that extremely low (fM-nM) concentrations of opioids can rapidly prolong the APD of DRG neurons (see Shen and Crain, *Brain Res.*, Vol. 491, pp. 227–242 (1989) and Crain and Shen *Trends Pharmacol. Sci.*, Vol. 11, pp. 7–81 (1990)), tests were carried out to evaluate possible opioid mediation of the NGF-induced APD prolongation.

FIG. 2 demonstrates that pretreatment of DRG neurons with the opioid receptor antagonist naloxone (NLX) or the specific kappa opioid receptor antagonist nor-binaltorphimine (nor-BNI) blocks NGF-induced APD prolongation, whereas mu and delta opioid antagonists are ineffective. FIG. 2A, records 1 and 2 show that APD of a DRG neuron is prolonged by the application of 0.1 nM NGF (as in FIG. 1, records 1 and 2). FIG. 2A, record 3 shows that after BSS rinse and introduction of 10 nM NLX, APD shortens and is then stably maintained (for about 15 minutes) prior to additional tests. FIG. 2A, record 4 shows that the application of 0.1 nM NGF in the presence of NLX is no longer effective in prolonging the APD. In contrast, FIG. 2B, records 1 and 2 show that the application of NGF (1 nM) to another DRG neuron in the presence of the delta opioid antagonist naltrindole (NTI, 10 nM, 7 minute pretreatment) is still effective in prolonging the APD. FIG. 2B, records 3 and 4 show that the mu opioid antagonist β-funaltrexamine (β-FNA, 10 nM, 10 minute pretreatment) is also ineffective in blocking the NGF-induced APD prolongation of this neuron. However, as shown in FIG. 2B, records 5 and 6, in the presence of the kappa opioid antagonist, nor-BNI (10 nM; 10 minute pretreatment), 1 nM NGF is no longer able to prolong the APD of this same neuron.

Pretreatment of DRG neurons with naloxone (10 nM) prevented NGF-induced prolongation of the APD in 15 out of 18 cells (see FIG. 2A, records 3 and 4), whereas the "inactive" enantiomer, (+)naloxone (10 nM), was ineffective in blocking NGF-induced APD prolongation of these cells (n=4). The specificity of the anti-NGF receptor antibody preparation was controlled by tests showing that anti-NGFR (5 µg/ml) did not block exogenous opioid-induced APD prolongation (tested with 1 nM dynorphin or DADLE; 4 out of 6 cells).

These results led the inventors to the hypothesis that NGF might stimulate the release of endogenous opioid from DRG neurons which, in turn, could activate excitatory opioid receptors on the same cells, thereby resulting in APD prolongation. This hypothesis was strengthened by additional tests with antagonists of specific mu, delta and kappa opioid receptors. Nor-binaltorphimine (10 nM), a specific kappa antagonist, blocked NGF-induced APD prolongation in 10 out of 12 DRG neurons (see FIG. 2B, records 5 and 6), whereas the mu and delta antagonists, beta-funaltrexamine and naltrindole (10–100 nM) were ineffective (n=12) (see FIG. 2B, records 1–4). These pharmacologic tests suggest that NGF may prolong the APD of DRG neurons by stimulating release of specific opioids that activate excitatory kappa opioid receptors on these cells.

Figure 3A:
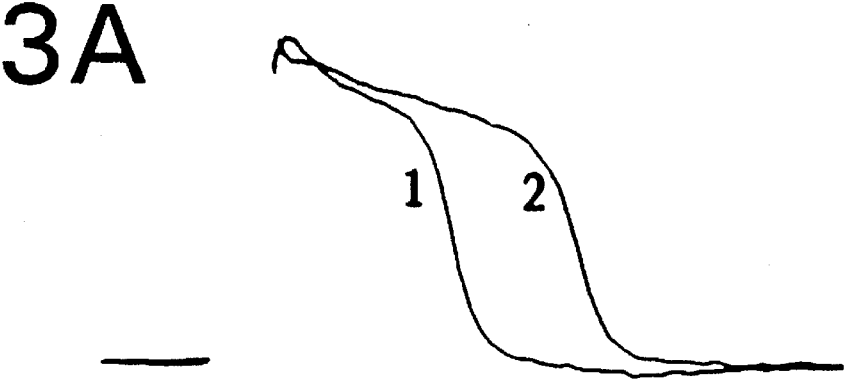
FIG. 3 is comprised of FIG. 3A and FIG. 3B.
Figure 3B:
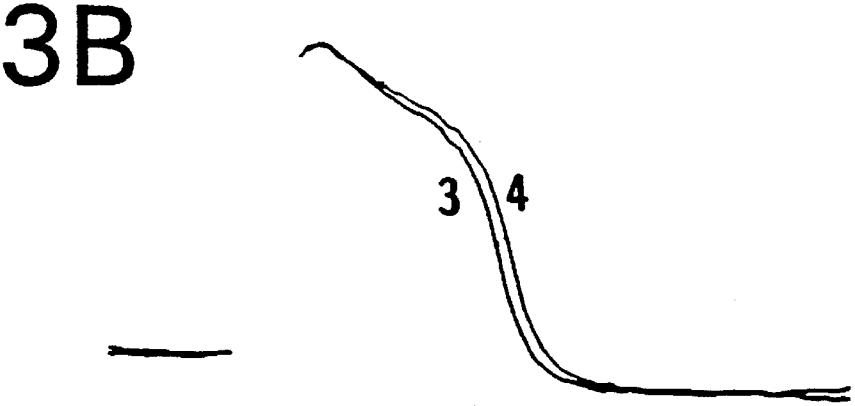
Figure 3C:
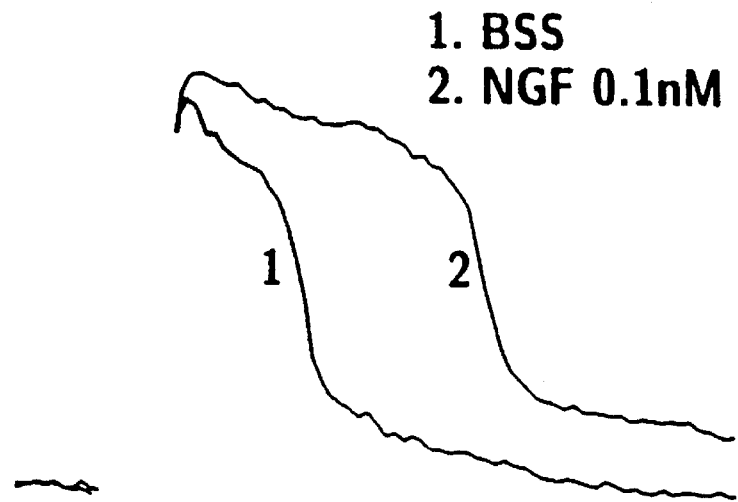
Figure 3D:
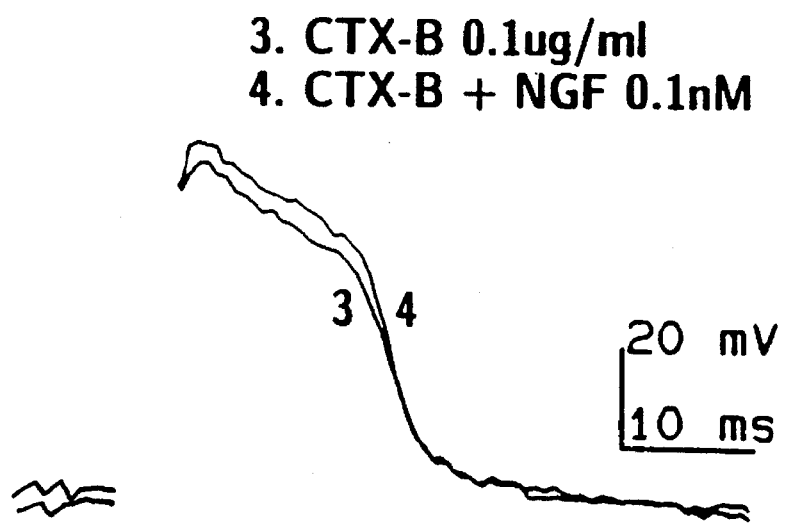

The inventors have also discovered that treatment of DRG neurons with cholera toxin A or B subunit blocks NGF-induced opioid-mediate APD prolongation. Further evidence consonant with mediation of NGF-induced APD prolongation by secondarily activated excitatory opioid receptors was obtained by pretreating the cells with cholera toxin-A subunit (CTX-A) and cholera toxin-B subunit (CTX-B). It was previously shown that APD prolongation elicited in DRG neurons by application of low (<nM) concentrations of exogenous opioid agonists could be prevented by pretreatment with CTX-A, which interferes with Gs-coupling of these excitatory opioid receptors to adenylate cyclase (see Shen and Crain, Brain Res., Vol. 525, pp. 225–231 (1990)) or with CTX-B, which interferes with GM1 ganglioside-regulation of these receptors (see Shen and Crain, Brain Res., Vol. 531, pp. 1–7 (1990) and Shen and Crain, Brain Res., Vol. 559, pp. 130–138 (1991)). Pretreatment of DRG neurons with CTX-A (0.1 µg/ml; >15 minutes) blocked NGF-induced APD prolongation (12 out of 12 cells; see FIG. 3A), just as it blocked exogenous opioid-induced excitatory effects. Similarly, pretreatment of DRG neurons with CTX-B (0.1 µg/ml; >15 minutes) also blocked NGF-induced prolongation (6 out of 6 cells; see FIG. 3B), just as it blocks exogenous opioid-induced excitatory effects.

FIG. 3 demonstrates that pretreatment of DRG neurons with cholera toxin A or B subunit blocks NGF-induced opioid-mediated APD prolongation by interfering with Gs-coupling of excitatory opioid receptors to adenylate cyclase or by interfering with GM1 ganglioside-regulation of these receptors, respectively. FIG. 3A, records 1 and 2 show that the APD of a DRG neuron is prolonged by 0.1 nM NGF. FIG. 3A, record 3 shows that after BSS rinse and introduction of 0.1 µg/ml CTX-A, APD shortens and is stably maintained (for about 7 minutes) prior to additional tests. FIG. 3A, record 4 shows that the application of 0.1 nM NGF in the presence of CTX-A is no longer effective in prolonging the APD. FIG. 3B, records 1 and 2 show that the APD of another DRG neuron is prolonged by 0.1 nM NGF. FIG. 3B, record 3 shows that after BSS rinse and introduction of 0.1 µg/ml CTX-B, APD shortens and is then stably maintained (for about 10 minutes) prior to additional tests. FIG. 3B, record shows that the application of 0.1 nM NGF in the presence of CTX-B is no longer able to prolong the APD of this neuron.

These data demonstrate that remarkably low (pM) concentrations of NGF can rapidly prolong the APD of mouse sensory neurons. These NGF-induced excitatory effects are blocked by pretreatment of the DRG neurons with monoclonal antibodies to rodent NGF receptors. They are also prevented by the opioid receptor antagonist, naloxone. On the other hand, anti-NGF receptor antibody treatment did not block APD prolongation elicited by exogenous opioids. These results suggest that NGF may directly stimulate the release of endogenous opioid from DRG neurons and that prolongation of the APD occurs secondarily by activation of high-affinity excitatory opioid receptors on these same or nearby cells. However, these data do not preclude the possibility that small amounts of opioid may be tonically released from DRG neurons which do not reach threshold levels for evoking excitatory opioid receptor-mediated APD prolongation unless their effects are enhanced by a synergistic NGF-induced stimulatory effect on the Gs-coupled opioid second messenger system.

In addition, NGF-induced prolongation of the APD is blocked by the specific kappa opioid receptor antagonist nor-binaltorphimine, whereas the specific mu and delta opioid receptor antagonists beta-funaltrexamine and naltrindole were ineffective. These pharmacologic analyses suggest that NGF may stimulate the release of an opioid that selectively activates kappa excitatory opioid receptors. The electrophysiologic results are remarkably consonant with radio-immunological and immuno-histochemical studies demonstrating that significant concentrations of opioid peptides, especially the kappa opioid, dynorphin, are present in many types of sensory ganglion neurons, both in perikarya as well as in axons, dorsal roots and peripheral terminals.

Sensory neurons have been shown to release Substance P in response to noxious stimuli in vivo (see Jessel et al., Nature, Vol. 268, pp. 549–551 (1977); Helme et al., Neurosci. Lett., Vol. 8, pp. 463–471 (1986); and Duggan et al., Brain Res., Vol. 403, pp. 345–349 (1987)) and during electrical, high-K$^+$ or PGE$_2$-stimulation in culture (see Mudge et al., Proc. Nat'l. Acad. Sci. USA, Vol. 76, pp. 526–530 (1979); Holz et al., J. Neurosci., Vol. 8, pp. 463–471 (1988); and Waite et al., Soc. Neurosci. Abstr., Vol. 18, p. 690 (1992)), and to release PGI$_2$ (prostacyclin) by application of bradykinin or ionomycin in culture (see Basbaum et al., J. Neurosci., Vol. 6, pp. 127–133 (1986)). However, no evidence of the release of opioids from sensory DRG neurons has been reported. In order to obtain more direct evidence that NGF-induced APD prolongation is mediated by NGF-stimulated release of opioids, the perfusate collected from DRG-cord explants after exposure to NGF (0.1 nM, 5 minutes) was tested. Preliminary tests indicated that this perfusate could prolong the APD of anti-NGFR-treated DRG neurons.

The blockade of NGF-induced prolongation of the APD of DRG neurons by low concentrations of CTX-A as well as CTX-B initially suggested possible Gs-coupling and GM1 ganglioside-regulation of the NGF receptors mediating these excitatory effects. However, it is more likely that these results are due to the blocking effects of CTX-A and CTX-B on the secondarily activated excitatory opioid receptor functions, similar to the actions of these toxin components in preventing exogenous opioid-induced APD prolongation. Furthermore, no evidence of direct NGF receptor-coupling to Gs or Gi has been detected.

The monoclonal antibodies to rat NGF receptors used in the present study to block NGF-induced prolongation of the APD of DRG neurons presumably bind to "low-affinity" NGF receptors (see Chandler et al., *J. Biol. Chem.*, Vol. 259, pp. 649–663 (1984) and Westcamp et al., *Neuron*, Vol. 6, pp. 649–663 (1991)), recently termed $p75^{NGFR}$ (see Hempstead et al., *Nature*, Vol. 6, pp. 649–663 (1991) and Meakin et al., *Trends Neurosci.*, Vol. 15, pp. 323–331 (1992)). Further studies with antibodies to the high-affinity trk receptors for NGF, e.g., $p140^{prototrk}$ (Kaplan et al., *Science*, Vol. 252, pp. 554–558 (1991)) may clarify the degree to which the proposed NGF-induced release of opioid is mediated directly by $p75^{NGFR}$ receptors or by activation of low-affinity NGF receptors that are functionally linked to trk receptors.

In the present invention, the electrophysiologic evidence of NGF-induced opioid-mediated excitatory effects on DRG neurons in culture may clarify cellular mechanisms underlying the hyperalgesia observed after intravenous administration of NGF in adult mice and the heat hyperalgesia that has recently been shown to occur within 10 minutes after injection of NGF (1 µg/g; IP) in adult rats (see Lewin et al., *J. Neurosci.*, Vol. 13, pp. 2136–2148 (1993)). The relevance of opioid-induced excitatory prolongation of the APD of DRG neurons in culture to hyperalgesia in vivo is suggested by studies with an animal model of persistent pain in arthritic rats where exceedingly low doses of morphine elicited a naloxone-reversible paradoxical hyperalgesia (see Kayser et al., *Brain Res.*, Vol. 414, pp. 155–157 (1987)). Furthermore, evidence has been reported of naloxone-reversible hyperalgesia mediated by activation of kappa opioid receptors on neurons in the brainstem and cervical spinal cord (see Wu et al., *Life Sci.*, Vol. 33, pp. 1831–1838 (1983) and Hamann et al., *J. Pharmacol. Exp. Ther.*, Vol. 261, pp. 707–715 (1992)). The excitatory effect of low concentrations of dynorphin and other kappa opioids on DRG neurons is also consonant with in vivo studies demonstrating "anti-analgesic" effects of extremely low intrathecal doses of dynorphin (about 0.05 fmol) in adult mice which can be blocked not only by the opioid receptor antagonists naloxone and nor-binaltorphimine (see Fujimoto et al., *J. Pharmacol. Exp. Ther.*, Vol. 251, pp. 1045–1052 (1989)), but also by intrathecal administration of anti-dynorphin antibodies (see Fujimoto et al., *Neuropharmacol.*, Vol. 29, pp. 609–617 (1989)) or cholera toxin (see Fujimoto et al., *FASEB J.*, Vol. 6, A1302 (1992) and Arts et al., *Pharmacol. Biochem. Behav.*, In Press (1993)).

Since it has been discovered by the inventors that NGF-induced hyperalgesia is mediated by activation of kappa excitatory opioid receptors on nociceptive neurons, this can be prevented simply by pre-treatment with or co-administration of a selective opioid receptor antagonist. Hence, undesirable side-effects which arise during clinical use of exogenous NGF for treatment of taxol-induced and cisplatin-induced and diabetic sensory neuropathies as well as other neurologic disorders will be eliminated.

Tests on Rodents In Vivo

In order to show that the administration of nerve growth factor to rodents results in a rapid onset of thermal and mechanical hyperalgesia, hrNGF (Genentech) (5 mg/kg) was administered intraperitoneally to mice and rats. This resulted in a significant reduction (p<0.05 by ANOVA) in tail flick thresholds in both rats (3.82±0.2 seconds from control of 4.50±0.2 seconds) and mice (7.96±0.34 from control of 9.06±0.35). This suggests that nerve growth factor causes hypersensitivity to thermal stimulation.

Figure 4:
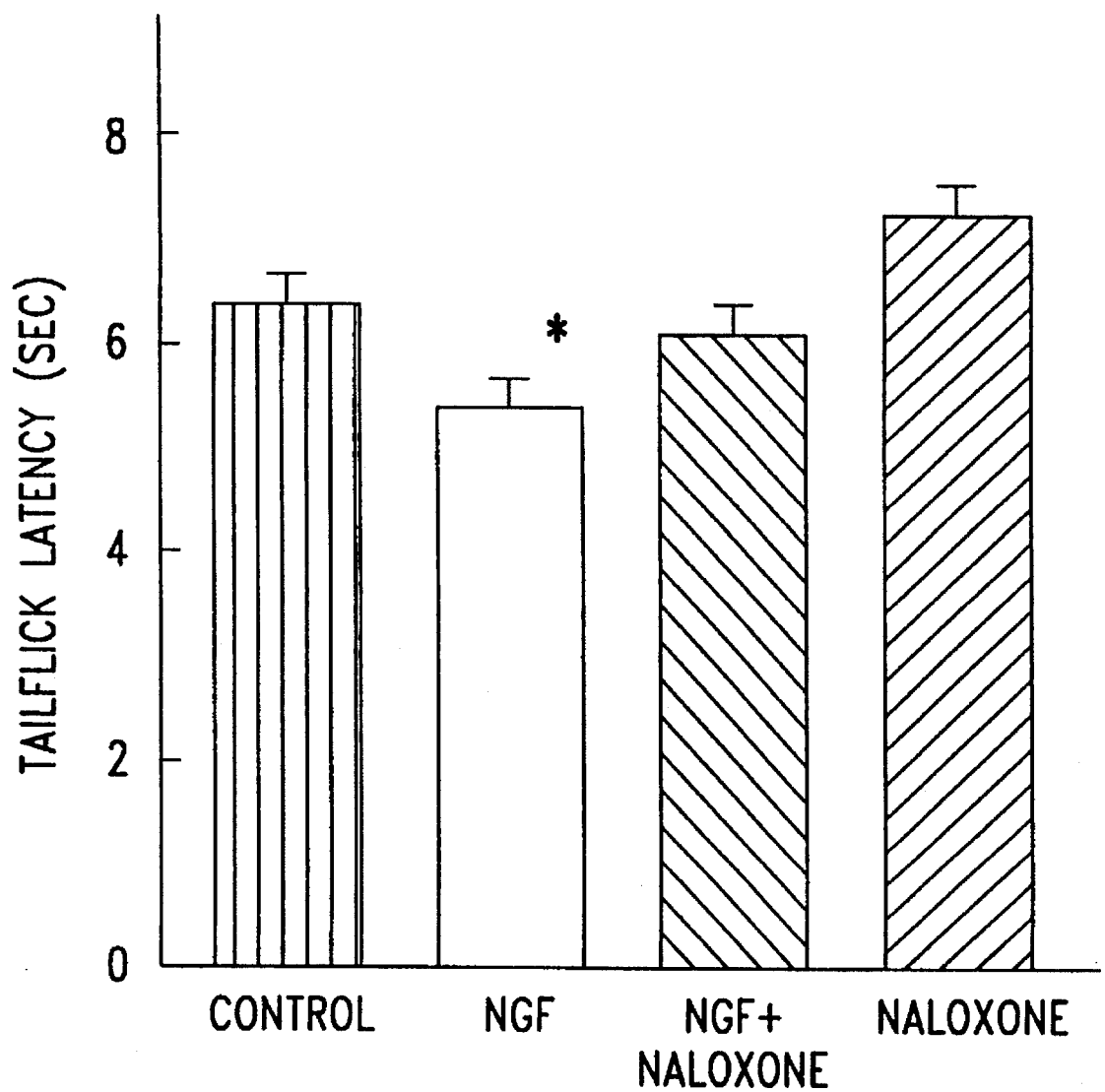
FIG. 4 represents measurements of tail flick latency in mice treated with nerve growth factor, nerve growth factor in combination with naloxone, and naloxone alone.
Figure 5:
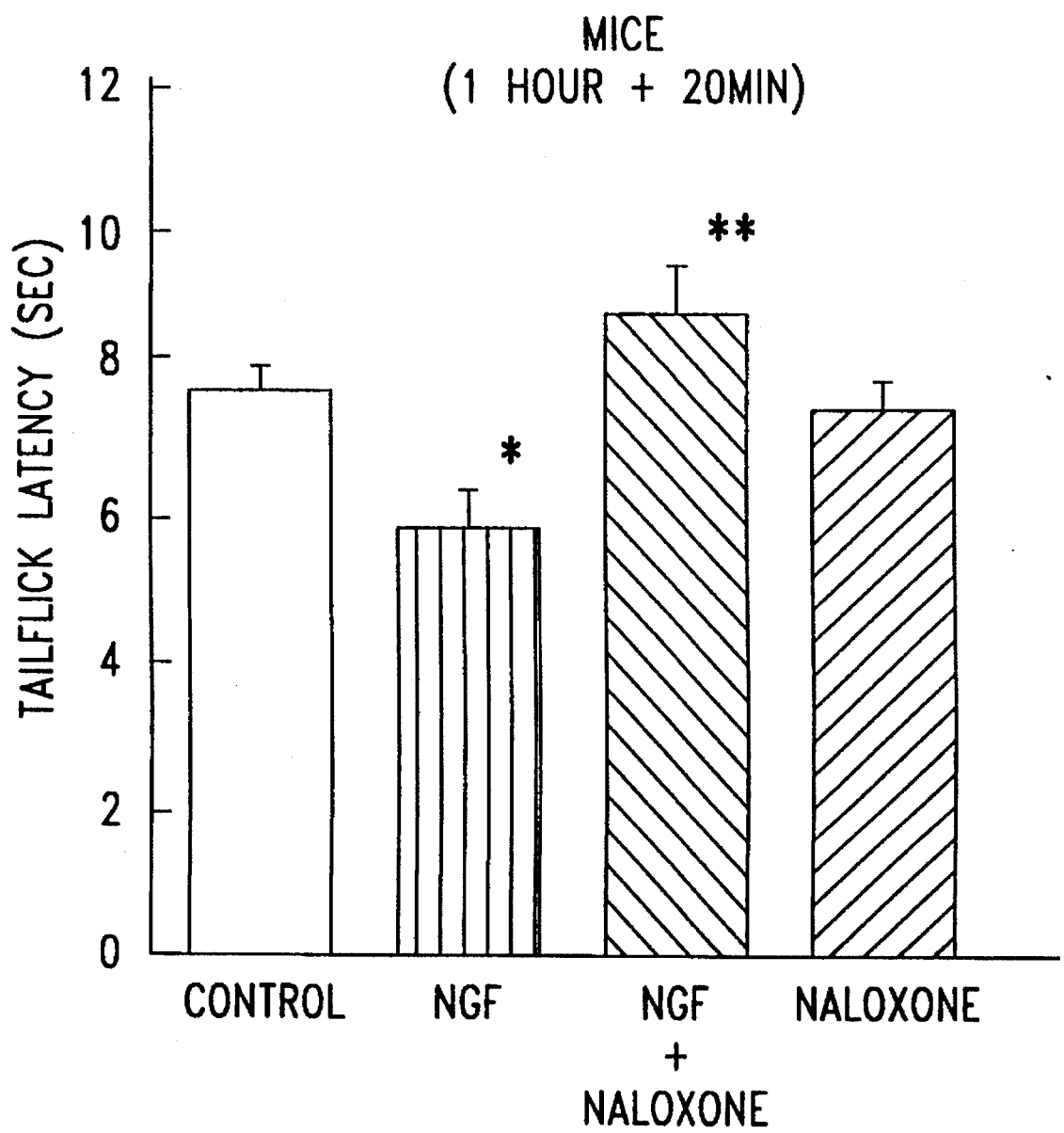
FIG. 5 represents measurements of tail flick latency 1 hour and 20 minutes after mice were treated with nerve growth factor, nerve growth factor in combination with naloxone and naloxone alone.
Figure 6:
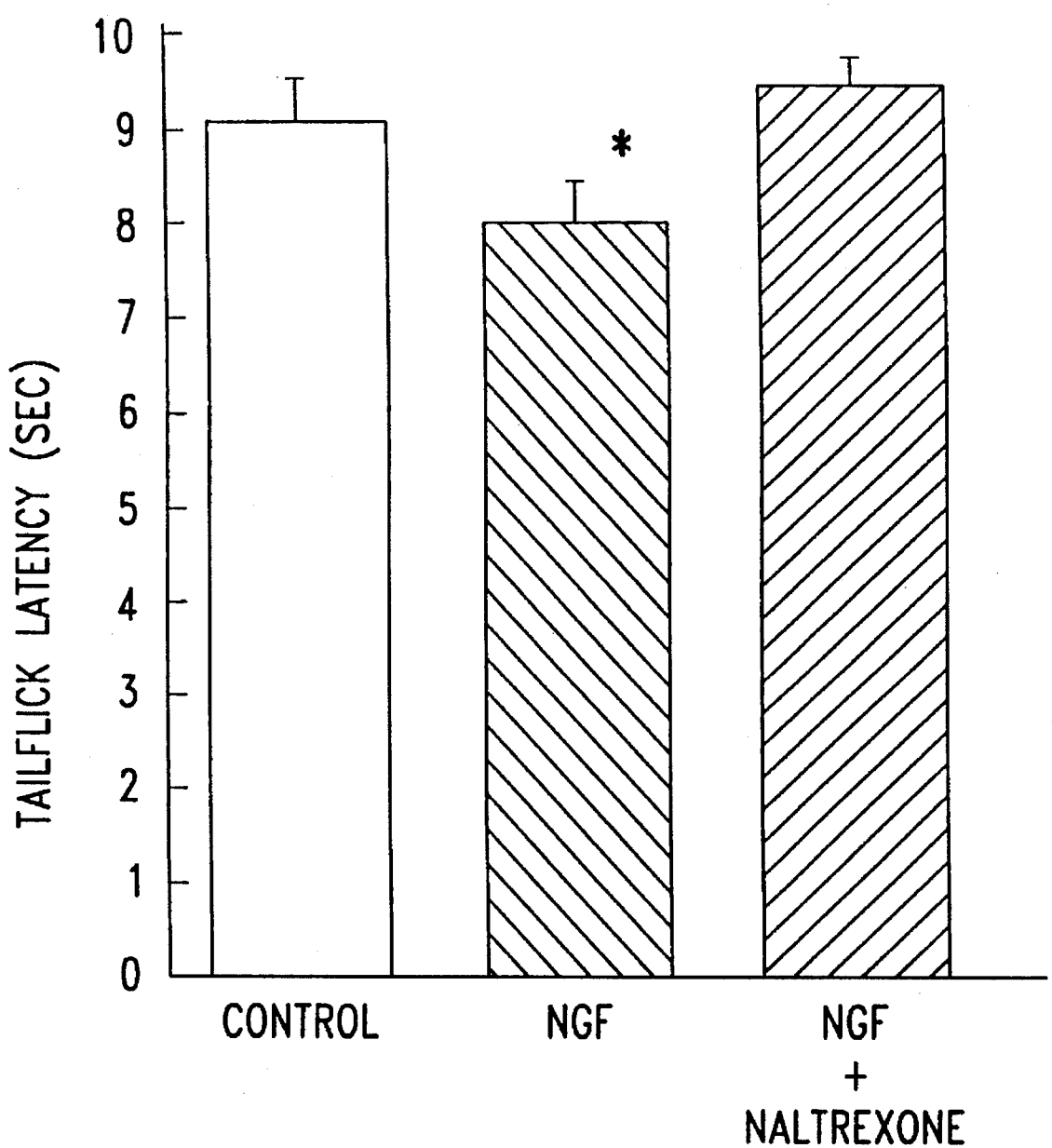
FIG. 6 represents measurements of tail flick latency in mice treated with nerve growth factor alone and nerve growth factor in combination with naloxone and naltrexone.
Figure 7:
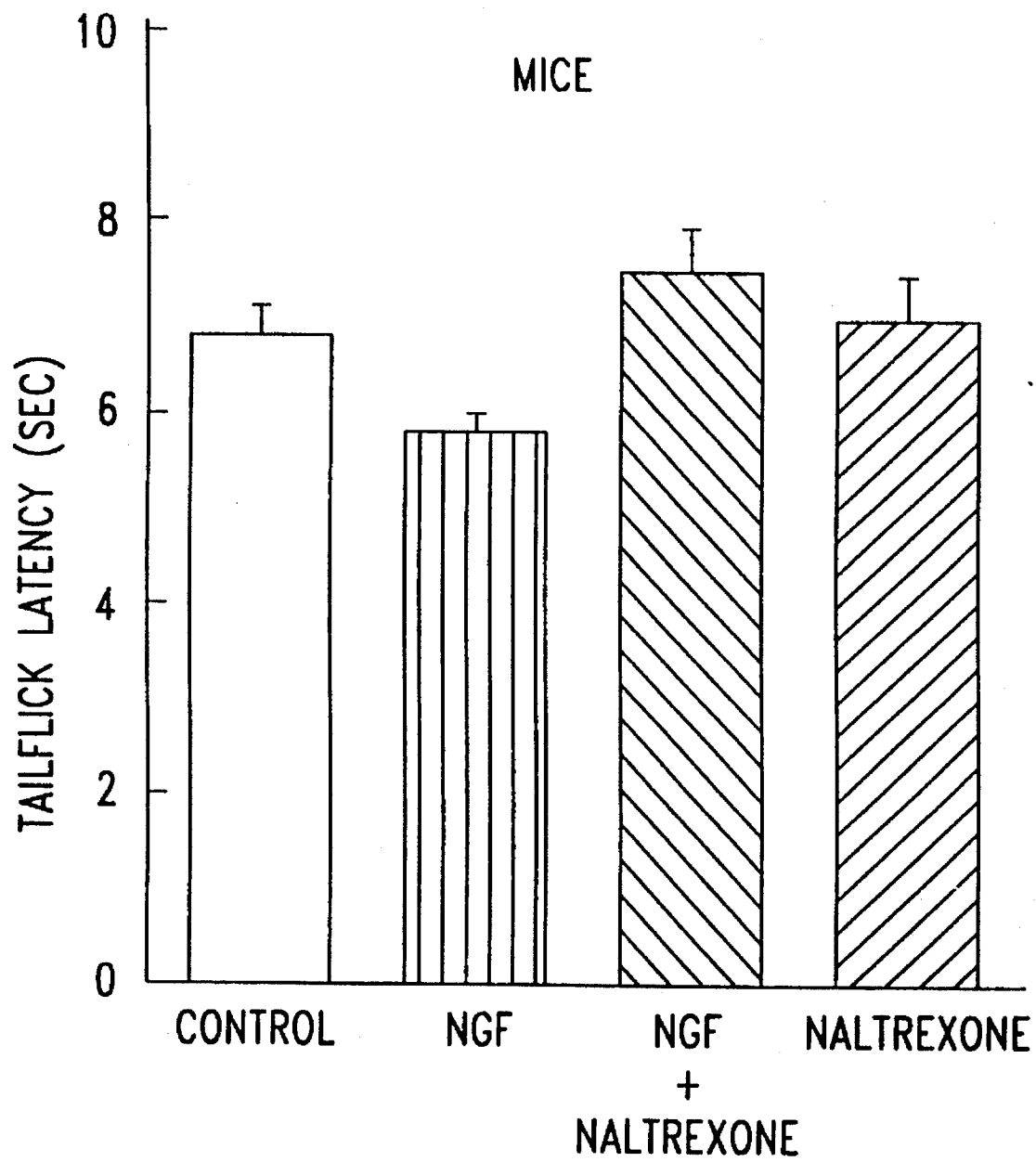
FIG. 7 represents measurements of tail flick latency in mice treated with nerve growth factor alone, nerve growth factor in combination with naltrexone and naltrexone alone.
Figure 8:
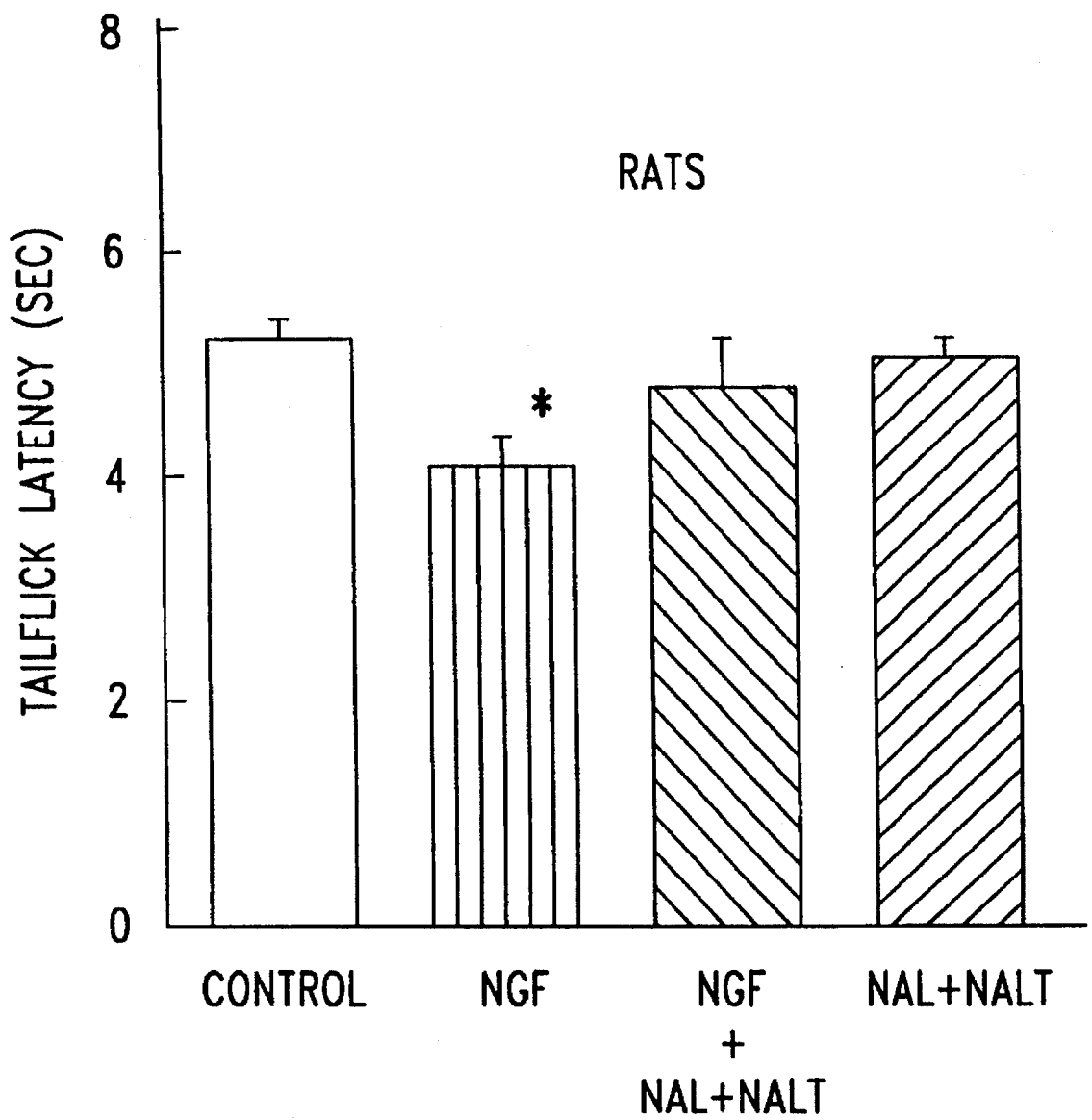
FIG. 8 represents measurements of tail flick latency in rats treated with nerve growth factor alone, nerve growth factor in combination with both naloxone and naltrexone, and naloxone in combination with naltrexone.

In order to block this hypersensitivity to thermal stimulation, the rats and mice were pretreated with the antagonists of the invention. As shown in FIGS. 4 and 5, pretreatment with nerve growth factor in combination with naloxone or naloxone alone (3 mg/kg in rats and 5 mg/kg in mice) resulted in the blocking of hypersensitivity to thermal stimulation. As shown in FIG. 6, pretreatment with nerve growth factor in combination with both naloxone (3 mg/kg in rats and 5 mg/kg in mice) and naltrexone (10 mg/kg in rats and 15 mg/kg in mice) completely prevented the reduction in tail flick latency in both rats and mice caused by the administration of nerve growth factor. As shown in FIGS. 7 and 8, pretreatment with nerve growth factor in combination with naltrexone, naltrexone alone, nerve growth factor in combination with both naloxone and naltrexone and naloxone plus naltrexone also resulted in the blocking of the reduction in tail flick latency in both mice and rats.

Figure 9:
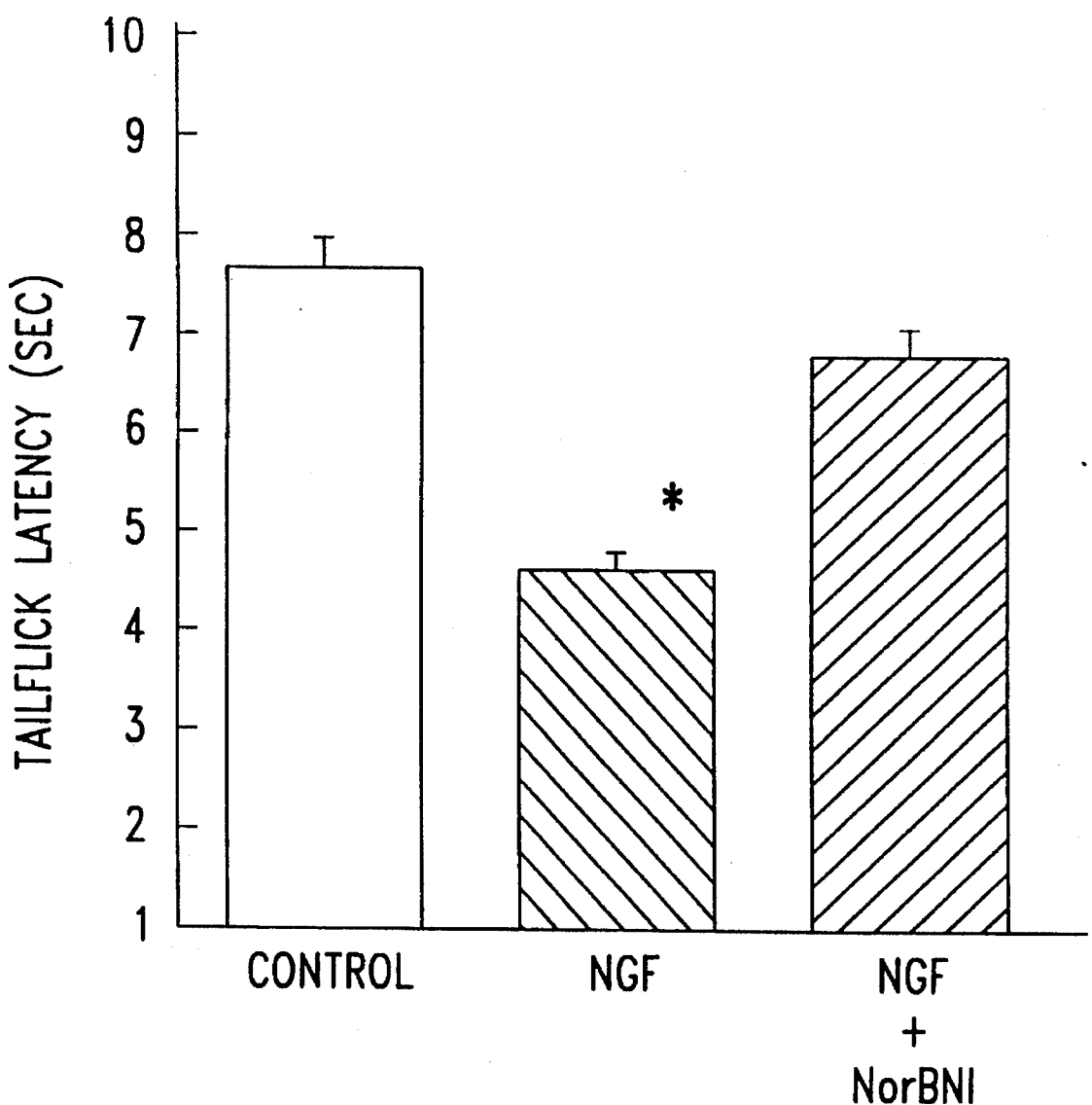
FIG. 9 represents measurements of tail flick latency in mice treated with nerve growth factor alone and nerve growth factor in combination with nor-binaltorphimine.

In order to determine whether this effect was mediated via the kappa opiate receptor subtype, the selective kappa blocker nor-binaltorphimine (0.1 mg/kg) was administered. As shown in FIG. 9, even at low doses, nor-binaltorphimine, when administered in combination with nerve growth factor, prevented nerve growth factor-induced hyperalgesia (p<0.05 ANOVA). These data provide evidence that nerve growth factor-induced release of kappa opiates, e.g., dynorphin, mediates thermal hyperalgesia.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. A method for attenuating nerve growth factor-induced hyperalgesia in a subject being treated with said nerve growth factor comprising administering to the subject prior to or in combination with said nerve growth factor treatment an amount of at least one excitatory opioid receptor antagonist effective to attenuate hyperalgesia induced by said nerve growth factor.

2. The method of claim 1 wherein the antagonist is selected from the group consisting of naloxone, naltrexone, nor-binaltorphimine, etorphine, dihydroetorphine, diprenorphine and cholera toxin A and B subunits.

3. The method of claim 1 wherein the excitatory opioid receptor antagonist is a kappa subtype opioid receptor antagonist.

4. The method of claim 2 wherein the antagonist is naloxone.

5. The method of claim 2 wherein the antagonist is naltrexone.

6. The method of claim 1 wherein the mode of administration is selected from the group consisting of sublingual, intramuscular, intradermal, subcutaneous, intraperitoneal, intraveneous and inhalation administration.

7. A composition comprising nerve growth factor and at least one excitatory opioid receptor antagonist.

8. The composition of claim 7 wherein the antagonist is selected from the group consisting of naloxone, naltrexone, nor-binaltorphimine, etorphine, dihydroetorphine, diprenorphine and cholera toxin A and B subunits.

* * * * *